(12) United States Patent
Herzog et al.

(10) Patent No.: US 10,494,336 B2
(45) Date of Patent: *Dec. 3, 2019

(54) MONOMER FOR COPOLYMERIZATION WITH ALKENES, DIENES, VINYL COMPOUNDS AND/OR VINYLIDENE COMPOUNDS, METHOD FOR THE SYNTHESIS OF A COPOLYMER, COPOLYMER, RUBBER MIXTURE AND USE THEREOF

(71) Applicant: Continental Reifen Deutschland GmbH, Hannover (DE)

(72) Inventors: Katharina Herzog, Harsum (DE); Lena Mueller, Lauenhagen (DE); Carla Recker, Hannover (DE); Noa Pruss, Frankfurt (DE); Cathrin Sonja Conrad, Eschborn (DE); Phillipp Vana, Bad Gandersheim (DE)

(73) Assignee: Continental Reifen Deutschland GmbH, Hannover (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/810,639

(22) Filed: Nov. 13, 2017

(65) Prior Publication Data

US 2018/0065928 A1    Mar. 8, 2018

Related U.S. Application Data

(63) Continuation of application No. PCT/EP2016/060383, filed on May 10, 2016.

(30) Foreign Application Priority Data

May 12, 2015 (DE) .......... 10 2015 208 813

(51) Int. Cl.
C07C 381/04 (2006.01)
B29B 7/74 (2006.01)
(Continued)

(52) U.S. Cl.
CPC .......... *C07C 381/04* (2013.01); *B29B 7/7495* (2013.01); *B60C 1/0016* (2013.01);
(Continued)

(58) Field of Classification Search
CPC ........ C07C 381/04; C08F 12/14; C08F 12/30; C08F 212/14
See application file for complete search history.

(56) References Cited

U.S. PATENT DOCUMENTS 2,947,731 A    8/1960  Nummy
3,162,665 A *  12/1964  Szabo .................. C07C 381/04
                                                    560/307
(Continued)

FOREIGN PATENT DOCUMENTS

DE    102005044997 A1    3/2007
EP         0034020 A1    8/1981
(Continued)

OTHER PUBLICATIONS

English translation of International Search Report dated Jun. 30, 2016 of international application PCT/EP2016/060383 on which this application is based.

(Continued)

*Primary Examiner* — Ling Siu Choi
*Assistant Examiner* — David L Miller
(74) *Attorney, Agent, or Firm* — David L. Cate; Gregory Adams

(57) ABSTRACT

Disclosed are monomers for copolymerization with alkenes, dienes, vinyl compounds, and/or vinylidene compounds, a process for preparing a copolymer, a copolymer prepared by (Continued)

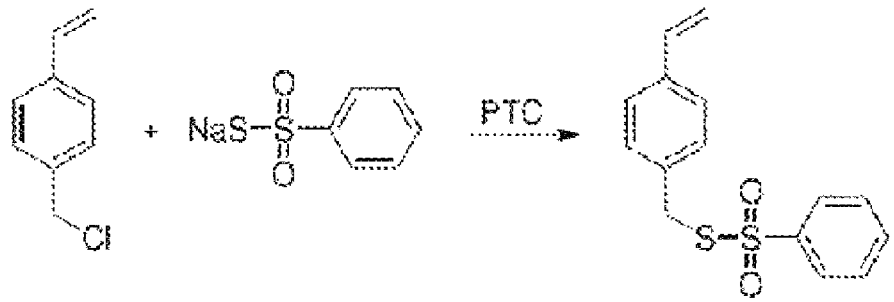

Schematic diagram of the synthesis of 4-vinylbenzenethiosulfonate the process, a sulfur-crosslinkable rubber mixture, and the use of the sulfur-crosslinkable rubber mixture for production of motor vehicle tires. In one embodiment, the monomer has the formula A-S—P, wherein A is a chemical group containing at least one C=C aliphatic double bond, S is a sulfur atom, and P is a protecting group.

5 Claims, 1 Drawing Sheet

(51) Int. Cl.
    *C08F 12/30* (2006.01)
    *C08F 12/32* (2006.01)
    *C08F 212/08* (2006.01)
    *B60C 1/00* (2006.01)
    *C08F 212/32* (2006.01)
    *C08F 112/14* (2006.01)
    *C08F 12/14* (2006.01)
    *C08F 212/14* (2006.01)

(52) U.S. Cl.
    CPC .............. *C08F 12/30* (2013.01); *C08F 12/32* (2013.01); *C08F 212/08* (2013.01); *C08F 212/32* (2013.01); *C08F 12/14* (2013.01); *C08F 112/14* (2013.01); *C08F 212/14* (2013.01); *Y02P 20/55* (2015.11)

(56) References Cited

U.S. PATENT DOCUMENTS

| | | | |
|---|---|---|---|
| 3,686,323 | A | 8/1972 | Brodnitz et al. |
| 4,483,960 | A | 11/1984 | Agarwal et al. |
| 7,968,633 | B2 | 6/2011 | York et al. |
| 7,968,634 | B2 | 6/2011 | York et al. |
| 7,968,635 | B2 | 6/2011 | York et al. |
| 7,968,636 | B2 | 6/2011 | York et al. |
| 8,182,626 | B2 | 5/2012 | Recker et al. |
| 8,252,863 | B2 | 8/2012 | Hasse et al. |
| 8,394,887 | B2 | 3/2013 | Yamauchi et al. |
| 2003/0013830 | A1 | 1/2003 | Blevins et al. |
| 2010/0108239 | A1 | 5/2010 | Recker et al. |
| 2010/0112259 | A1 | 5/2010 | Cruse et al. |
| 2010/0113681 | A1 | 5/2010 | O Brien et al. |
| 2013/0131240 | A1 | 5/2013 | Uekita et al. |
| 2018/0066094 | A1 | 3/2018 | Herzog et al. |

FOREIGN PATENT DOCUMENTS

| | | |
|---|---|---|
| GB | 1355106 A | 6/1974 |
| JP | 8-143627 A | 6/1996 |
| JP | 2006199827 A | 8/2006 |
| WO | 9909036 A1 | 2/1999 |
| WO | 2010059363 A1 | 5/2010 |
| WO | 2010059402 A1 | 5/2010 |

OTHER PUBLICATIONS

Duong, H. et al, "Acid Degradable and Biocompatible Polymeric Nanoparticles for the Potential Codelivery of Therapeutic Agents", Macromolecules, vol. 44, No. 20, Oct. 25, 2011, pp. 8008-8019, XP055282880.
Kozikowski, A. et al, "Chemistry of the Main Group Metals: A Stereoselective Synthesis of Allyl Vinyl Thioethers for the Thio-Claisen Reaction", Journal of Organometallic Chemistry, vol. 164, No. 2, Jan. 1, 1979, pp. C33 to C37, XP055167859.
English translation of International Search Report dated Jul. 19, 2016 of co-pending international application PCT/EP2016/060381.
Gonzalez-Fernandez, D. et al, "Copolymers with acetyl-protected thiol pendant groups as highly efficient stabilizing agents for gold surfaces", RSC Advances: An International Journal to Further the Chemical Sciences, Bd. 5, Nr. 18, Jan. 1, 2015, pp. 13722 to 13726, XP055287489.
Wulff, G. et al., "Enzyme-Analogue Built Polymers. IX.1 Polymers with Mercapto Groups of Definite Cooperativity", Israel Journal of Chemistry, vol. 17, 1978, pp. 291-297.
Muller E: Methoden der Organischen Chemie (Houben-Weyl), Band III, Physikalische Forschungsmethoden, Teil 1.4. Auflage. Stuttgart Georg Thieme Verlag, 1955, S. 153-155-978-3-13-1995504-9.

* cited by examiner

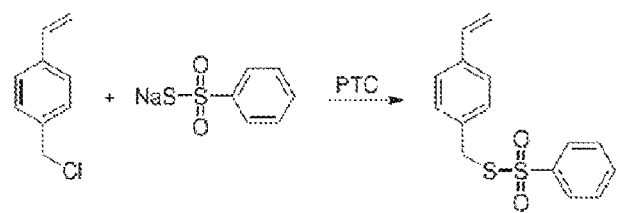
Schematic diagram of the synthesis of 4-vinylbenzenethiosulfonate

MONOMER FOR COPOLYMERIZATION WITH ALKENES, DIENES, VINYL COMPOUNDS AND/OR VINYLIDENE COMPOUNDS, METHOD FOR THE SYNTHESIS OF A COPOLYMER, COPOLYMER, RUBBER MIXTURE AND USE THEREOF

CROSS REFERENCE TO RELATED APPLICATIONS

This application is a continuation application of international patent application PCT/EP2016/060383, filed May 10, 2016, designating the United States and claiming priority from German application 10 2015 208 813.8, filed May 12, 2015, and the entire content of both applications is incorporated herein by reference.

FIELD OF THE INVENTION

Disclosed are monomers for copolymerization with alkenes, dienes, vinyl compounds, and/or vinylidene compounds, a process for preparing a copolymer, a copolymer prepared by the process, a sulfur-crosslinkable rubber mixture, and the use of the sulfur-crosslinkable rubber mixture for production of motor vehicle tires, cords, belts, and hoses.

BACKGROUND OF THE INVENTION

Copolymers, for example styrene-butadiene rubber, are used in sulfur-crosslinkable rubber mixtures in order to influence properties such as the abrasion characteristics and/or the tear properties and/or the rolling resistance characteristics. However, the structure of node formation in sulfur vulcanization is very substantially a matter of chance. As a result, said properties cannot be specifically influenced and improved as desired.

SUMMARY OF THE INVENTION

Disclosed are monomers for copolymerization with alkenes, dienes, vinyl compounds, and/or vinylidene compounds, such that the copolymers prepared in a vulcanized rubber mixture achieve an improvement in abrasion characteristics, tear properties, and/or rolling resistance characteristics.

This object is achieved by a monomer of formula I):

A-S—P    I)

where A is a chemical group containing at least one C═C aliphatic double bond, and
where S is a sulfur atom, and
where P is a protecting group selected from the group consisting of
S(═O)$_2$—R$^1$ with R$^1$=alkyl, benzyl or phenyl and/or
S—C(═S)—N—R$^2$R$^3$ with R$^2$ and R$^3$=alkyl, benzyl or phenyl and/or
N—R$^5$R$^6$ with R$^5$=hydrogen atom (H), alkyl, benzyl or phenyl and
R$^6$=alkyl, benzyl or phenyl.

The disclosed monomers thus have: a) at least one double bond that can take part in a polymerization, and b) a protected mercapto group which is deprotected at a later stage in the vulcanization of the polymers thus prepared, such that the sulfur atom of this mercapto group can take part in the vulcanization. In this way, the node structure of the sulfur vulcanizates prepared with the copolymer can be better adjusted as compared with the prior art, which has a positive effect on the abrasion characteristics, the tear properties, and/or the rolling resistance characteristics of the rubber mixture.

The R$^1$ to R$^6$ radicals in the protecting group P that are mentioned in formula I) can, as detailed above, be alkyl groups having 1 to 10 carbon atoms. In addition, O=oxygen atom, and N=nitrogen atom.

The A group is a chemical group containing at least one aliphatic double bond, for instance at least one terminal double bond, i.e. vinylic double bond. In this context, all chemical groups having at least the feature of the aliphatic, for instance terminal, vinylic C═C double bond are conceivable in principle. A double bond of this kind is suitable for taking part in a polymerization, which means that the compound of formula I) is a suitable monomer for a later copolymer.

As used herein, "double bond" is understood to mean a carbon-carbon double bond, i.e. C═C, unless explicitly referred to otherwise.

In one embodiment A is a 4-vinylbenzyl group.

BRIEF DESCRIPTION OF THE DRAWING

FIG. 1 shows a schematic diagram of the synthesis of 4-vinylbenzenethiosulfonate:

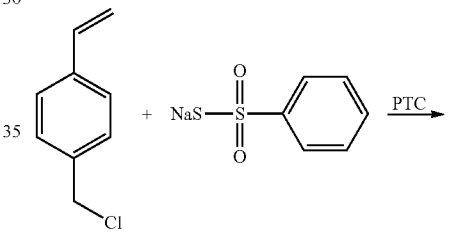

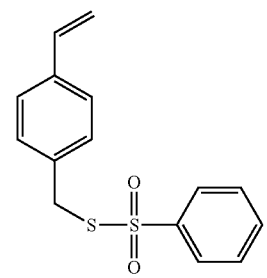

DESCRIPTION OF THE PREFERRED EMBODIMENTS OF THE INVENTION

In one embodiment, the monomer is 4-vinylbenzyl benzenethiosulfonate, where A is a 4-vinylbenzyl group and P is S(═O)$_2$—R$^1$, wherein R$^1$ is a phenyl group.

This compound thus has the formula II):

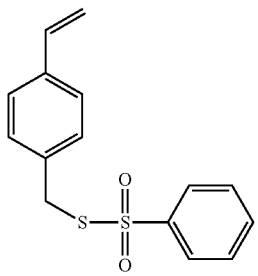

II)

The monomer of formula II), i.e. 4-vinylbenzyl benzenethiosulfonate (abbreviated to ViBSuT), is prepared by the following process. ViBSuT is synthesized in strongly polar solvents such as, for instance, water, ethanol, and/or DME, since the sodium benzenethiosulfonate could otherwise not be fully dissolved in an appropriate amount of solvent.

For instance, strongly polar solvents having a high dielectric constant or dielectric conductivity ε (also called permittivity) can be used, as a result of which they have a dissociating effect on ion pairs and salts. Strongly polar solvents can be protic, meaning that they have a functional group from which hydrogen atoms in the molecule can be eliminated as protons. Examples are water (ε=78), methanol, ethanol and other alcohols, carboxylic acids, such as formic acid or acetic acid, ammonia, and also primary and secondary amines, primary and secondary amides, such as formamide (ε=109), mineral acids, such as sulfuric acid or hydrogen halides or hydrohalic acids inter alia, or aprotic solvents that do not have sufficiently acidic hydrogen atoms that can be eliminated as protons. Examples are ethers, ketones, such as acetone, nitriles, such as acetonitrile, tertiary carboxamides, such as dimethylformamide (DMF), and sulfoxides, such as dimethyl sulfoxide (DMSO), inter alia.

Exemplary embodiments include 1,2-dimethoxyethane (DME), tetrahydrofuran (THF), diethyl ether (DEE), acetone, ethanol, methanol, water, acetic acid, dimethylformamide (DMF). In one embodiment, the polar solvent is 1,2-dimethoxyethane (DME), ethanol, water, acetic acid, and/or dimethylformamide (DMF).

The reaction is conducted in aqueous systems with the aid of a phase transfer catalyst (abbreviated to PTC). An exemplary scheme is shown in FIG. 1. Using toluene as solvent for the organic phase has the drawback of low product yields. The organic phase thus consists exclusively of the 4-vinylbenzyl chloride reactant. In addition to water, it is possible to use ethanol and 1,2-dimethoxyethane (DME, glyme) as strongly polar solvents in a phase transfer-catalyzed reaction.

EXAMPLE 1

A mixture of freshly distilled 4-vinylbenzyl chloride (9.71 g, 64.0 mmol, 1.0 eq.), sodium benzenethiosulfonate (25.14 g, 128.0 mmol, 2.0 eq.), Aliquat 336® (1.31 g, 3.2 mmol, 0.05 mol %), and water (320 mL) was stirred at 65° C. for 380 min. Subsequently, the reaction mixture was cooled down to room temperature and extracted with EtOAc (3×100 mL). The combined organic phases were washed with saturated NaCl solution, dried over MgSO$_4$, and concentrated under reduced pressure.

The crude product was purified by means of column chromatography on silica gel (hexane/EtOAc 20:1→0:1), and it was possible to isolate the monomer as a white solid in 95% purity (3.11 g, 10.7 mmol, 17%).

Also disclosed are processes for preparing a copolymer by free-radical copolymerization of an above-described monomer with at least one further monomer selected from the group consisting of: alkenes, dienes, vinyl compounds, and/or vinylidene compounds.

In the disclosed processes for preparing the copolymer, it is possible to employ all the standard free-radical methods, especially in solution, in emulsion and under RAFT conditions with RAFT-typical agents.

As used herein, the term "dienes," in accordance with Römpp Online, are understood to mean unsaturated aliphatic and cycloaliphatic hydrocarbons containing two double bonds in the molecule. The two double bonds can be conjugated. The conjugated diene can be selected from one or more of: 1,3-butadiene (butadiene), 2-methylbuta-1,3-diene (isoprene=2-($C_1$-$C_5$-alkyl)-1,3-butadiene, 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene, 1,3-cyclooctadiene, and/or 2-chloro-1,3-butadiene (chloroprene).

Exemplary dienes include isoprene, butadiene, and chloroprene.

Alkenes that can be involved in the polymerization as monomers are aliphatic compounds having a double bond, such as, for instance, ethene, propene, butene, pentene, and/or hexene.

The term "vinyl compound" as used herein encompasses all chemical compounds having at least one vinyl group, such as acrylates, methacrylates, acrylic acid, methacrylic acid, acrylonitrile, and vinylaromatic compounds.

In one embodiment, the vinyl compound comprises at least one vinyl compound that, apart from the vinyl group, has at least one further unsaturated group carbon group, such as, for instance, a double bond or an aromatic radical.

In another embodiment, the vinyl compound comprises at least one vinylaromatic compound.

As used herein, the term "vinylaromatic compound" encompasses monovinylaromatic compounds, i.e., compounds in which only one vinyl group is bound to an aromatic group, and vinylaromatic compounds in which two or more vinyl groups are bound to an aromatic group.

Any vinylaromatic compound known to those skilled in the art is conceivable as vinylaromatic compound. For example, the vinylaromatic compound is one or more of, styrene, $C_{1-4}$-alkyl-substituted styrenes, stilbene, vinylbenzyldimethylamine, 4-vinylbenzyl dimethylaminoethyl ether, N,N-dimethylaminoethylstyrene, tert-butoxystyrene, vinylpyridine, and/or divinylaromatic compounds.

The $C_{1-4}$-alkyl-substituted styrenes can be, for example, 2-methylstyrene, 3-methylstyrene, 4-methylstyrene, 2,4-dimethylstyrene, 2,4,6-trimethylstyrene, alpha-methylstyrene, 2,4-diisopropylstyrene, and/or 4-tert-butylstyrene.

The term "$C_{1-4}$-alkyl-substituted" as used herein means here that an alkyl radical having 1 to 4 carbon atoms is present as a substituent for a hydrogen atom.

The divinylaromatic compounds can be, for example, 1,2-divinylbenzene, 1,3-divinylbenzene, and/or 1,4-divinylbenzene.

As herein, the term "vinylidene compounds," in accordance with Römpp Online, are understood to mean chemical compounds having the atomic moiety $R_1R_2$=C=$CH_2$ bonded via a double bond, for example $Cl_2C$=$CH_2$ or $F_2C$=$CH_2$.

In one embodiment, the alkene is one or more of ethene, propene, butene, pentene, and/or hexene, and the diene is one or more of: 1,3-butadiene, 2-methylbuta-1,3-diene, 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene, 1,3-cyclooctadiene, and 2-chloro-1,3-butadiene, and the vinyl compound is an acrylate, methacrylates, acrylic acid, methacrylic acid, acrylonitrile, or a vinylaromatic compound selected from the group consisting of: styrene, 2-methylstyrene, 3-methylstyrene, 4-methylstyrene, 2,4-dimethylstyrene, 2,4,6-trimethylstyrene, alpha-methylstyrene, 2,4-diisopropylstyrene, 4-tert-butylstyrene, stilbene, vinylbenzyldimethylamine, 4-vinylbenzyl dimethylaminoethyl ether, N,N-dimethylaminoethylstyrene, tert-butoxystyrene, vinylpyridine, 1,2-divinylbenzene, 1,3-divinylbenzene, and/or 1,4-divinylbenzene.

The process for preparing a copolymer by free-radical copolymerization is described hereinafter using the example of the copolymerization of compound II), i.e. 4-vinylbenzyl benzenethiosulfonate (abbreviated to ViBSuT), with styrene.

The process is not limited to the illustrative monomers mentioned but can be used for preparation of all copolymers from the above-described monomers, including for preparation of copolymers from three or more different monomers.

The polymerization mixture had a starting concentration of 3.09 mol % of ViBSuT in relation to styrene (neglecting the impurities) and 0.05 mol % of AIBN. In this context, AIBN is the abbreviation for the chemical compound azobis(isobutyronitrile). The polymerization was effected at 60° C. over a period of 6 hours. The copolymer produced has a number-average molar mass (or molar mass distribution) Mn by GPC of 2350 g/mol and a polydispersity (Mw/Mn) of 2.74. Mw here is the weight-average molar mass distribution by GPC.

The sulfur content of the copolymer prepared was determined by means of elemental analysis, by means of which it was possible to determine the ratio of the monomers relative to one another, it being possible to rule out the presence of any large residual amounts of the 4-vinylbenzyl benzenethiosulfonate monomer, especially because there was no corresponding intensity to be found in the molar mass distribution. The desired copolymer was successfully synthesized.

For the determination of the molar mass or the molar mass distribution by means of GPC, the following measurement conditions were applied: SEC Analysis Systems 1260 Infinity from PSS Agilent with: PSS Agilent Technologies 1260 Iso Pump G1310B (HPLC pump), an Agilent 1260 ALS G1329B autosampler, an Agilent 1260 ALS injector, a precolumn (PSS SDV, 8×50 mm, particle size 5 µm), three separation columns (PSS SDV, 8×300 mm, particle size: 5 pore size $10^5$ (ten to the power of five) Å, $10^3$ (ten to the power of three) Å and $10^2$ (ten to the power of two) Å) and the detectors; PSS Agilent Technologies 1260 VWDVL UV detector at a wavelength of 310 nm and the PSS Agilent Technologies 1260 RID RI detector utilized; THF eluent (HPLC-grade) with toluene (>99.7%, dry) as internal standard (flow rate 1.0 mL/min at 35° C.). The system was calibrated with polystyrene standards having low polydispersity of PSS. For evaluation, the PSS WinGPC software was used. The detected intensities were standardized to 1 and, unless stated otherwise, were the signal from the RI detector.

Also provided are copolymers prepared by the disclosed processes. For example, the copolymer can be one of styrene and 4-vinylbenzyl benzenethiosulfonate that has been prepared as described above under free-radical polymerization conditions. Other exemplary comonomers (aside from the compounds I) or II)) are also described above.

The disclosed copolymers can also be a polymer of three or more different monomers. The disclosed copolymers can thus, for example, be a terpolymer of 4-vinylbenzyl benzenethiosulfonate, styrene, and butadiene.

In addition, it is possible to use two or more different monomers of formula I) having different protecting groups P, for example.

Disclosed herein are also sulfur-crosslinkable rubber mixtures comprising at least one of the copolymers prepared.

The sulfur-crosslinkable rubber mixtures disclosed herein comprise at least one of the copolymers prepared as described above and can also comprise at least one diene rubber known in the prior art.

Diene rubbers refer to rubbers that arise through polymerization or copolymerization of dienes and/or cycloalkenes, and hence have C=C double bonds either in the main chain or in the side groups.

The at least one diene rubber can be natural polyisoprene, synthetic polyisoprene, polybutadiene (butadiene rubber), unfunctionalized styrene-butadiene copolymer (styrene-butadiene rubber), epoxidized polyisoprene, styrene-isoprene rubber, halobutyl rubber, polynorbornene, isoprene-isobutylene copolymer, ethylene-propylene-diene rubber, nitrile rubber, chloroprene rubber, acrylate rubber, fluoro rubber, silicone rubber, polysulfide rubber, epichlorohydrin rubber, styrene-isoprene-butadiene terpolymer, hydrogenated acrylonitrile-butadiene rubber, and/or hydrogenated styrene-butadiene rubber.

In one embodiment, nitrile rubber, hydrogenated acrylonitrile-butadiene rubber, chloroprene rubber, butyl rubber, halobutyl rubber, or ethylene-propylene-diene rubber are used in the production of industrial rubber articles such as cords, belts, hoses, and/or shoe soles.

The terms "vulcanized" and "crosslinked" are used synonymously herein.

The disclosed rubber mixtures can further comprise at least one filler such as silica, carbon black, and optionally further known polar or nonpolar fillers, such as aluminosilicates, chalk, kaolin, starch, magnesium oxide, titanium dioxide, and/or rubber gels, and also carbon nanotubes (CNTs, including discrete CNTs, called hollow carbon fibers (HCFs) and modified CNTs containing one or more functional groups, such as hydroxyl, carboxyl and carbonyl groups), graphite, graphenes, and/or what is called "carbon-silica dual-phase filler".

If the filler is at least one silica, the rubber mixture can contain 1 to 300 phr, 1 to 200 phr, or 1 to 150 phr, of at least one silica.

If the filler is at least one carbon black, the rubber mixture can contain 1 to 200 phr, 1 to 170 phr, or 1 to 100 phr of at least one carbon black.

The silicas can be any silicas known to those skilled in the art that are suitable as filler for tire rubber mixtures. In one embodiment, for example, a finely divided precipitated silica having a nitrogen surface area (BET surface area) (in accordance with DIN ISO 9277 and DIN 66132) of 35 to 350 $m^2$/g, 60 to 260 $m^2$/g, or 120 to 230 $m^2$/g, and a CTAB surface area (in accordance with ASTM D 3765) of 30 to 400 m²/g, 60 to 250 m²/g, or 120 to 230 m²/g is used.

If the rubber mixture comprises carbon black, all types of carbon black known to those skilled in the art are conceivable. For instance, in one example, a carbon black having an iodine adsorption number to ASTM D 1510 of 30 to 180 g/kg or 30 to 130 g/kg, and a DBP number according to ASTM D 2414 of 80 to 200 mL/100 g, 100 to 200 mL/100 g, or 100 to 180 mL/100 g is used.

The rubber mixtures disclosed herein can also comprise a mixture of two or more of the fillers mentioned.

Zinc oxide as used herein does not count as one of the fillers, but is present in the disclosed rubber mixtures in combination with stearic acid.

In addition, the rubber mixtures disclosed herein can also comprise further additives. Further additives include—in addition to zinc oxide (ZnO) and stearic acid—optionally silane coupling agents for the binding of silica to the polymer chains of the rubbers present, plasticizers, the vulcanization system composed of sulfur and/or sulfur donors with the aid of vulcanization accelerators, antiozonants, aging stabilizers, tackifying resins, masticating aids, and, as well as ZnO and stearic acid, further activators or processing aids, for example fatty acid salts, for example zinc soaps and fatty acid esters and derivatives thereof, for example zinc stearate, or zinc complexes, for example zinc ethylhexanoate.

The silane coupling agents employed herein can be any silane coupling agent known to those skilled in the art for use in rubber mixtures. Additionally, it is possible to use one or more different silane coupling agents in combination with one another. The rubber mixture can thus contain a mixture of various silanes.

The silane coupling agents react with the surface silanol groups of the silica or other polar groups during mixing of the rubber or of the rubber mixture (in situ) or in a pretreatment (premodification) even before addition of the filler to the rubber. Such coupling agents known from the prior art are bifunctional organosilanes that have at least one alkoxy, cycloalkoxy, or phenoxy group as a leaving group on the silicon atom and have, as another functionality, a group that can, after dissociation, if appropriate, enter into a chemical reaction with the double bonds of the polymer. The latter group can, for example, be the following chemical groups: —SCN, —SH, —NH$_2$ or —S$_x$— (where x=2 to 8).

For instance, silane coupling agents used can, for example, be 3-mercaptopropyltriethoxysilane, 3-thiocyanatopropyltrimethoxysilane or 3,3'-bis(triethoxysilylpropyl) polysulfides having 2 to 8 sulfur atoms, e.g. 3,3'-bis(triethoxysilylpropyl) tetrasulfide (TESPT), the corresponding disulfide (TESPD), or else mixtures of the sulfides having 1 to 8 sulfur atoms with different contents of the various sulfides. TESPT can, for example, also be added as a mixture with industrial carbon black (trade name: X50S® from Evonik).

In one embodiment, a silane mixture comprising disulfides to an extent of 40% to 100% by weight, 55% to 85% by weight of disulfides, or 60% to 80% by weight of disulfides can be used. A mixture of this kind is available, for example, under the Si 261® trade name from Evonik, which is described, for example, in DE 102006004062 Al.

Blocked mercaptosilanes, as known, for example, from WO 99/09036, can also be used as a silane coupling agent. It is also possible to use silanes as described in U.S. Pat. Nos. 7,968,633; 7,968,636; 7,968,635; and, 7,968,634. It is possible to use, for example, silanes that are marketed under the NXT name (e.g. 3-(octanoylthio)-1-propyltriethoxysilane)

in a number of variants from Momentive, USA, or those that are marketed under the name VP Si 363® by Evonik Industries.

It is also conceivable that one of the abovementioned mercaptosilanes, especially 3-mercaptopropyltriethoxysilane, is used in combination with processing aids (that are listed below), especially PEG carboxylates.

In addition, the rubber mixture can comprise further activators and/or agents for the incorporation of fillers, especially carbon black. The latter may, for example, be the compound S-(3-aminopropyl)thiosulfuric acid as disclosed, for example, in U.S. Pat. App. Pub. No. 2013/0131240, and/or metal salts thereof, that give rise to very good physical properties of the rubber mixture especially in combination with at least one carbon black as filler.

The proportion by weight of the total amount of further additives is from 3 to 150 phr, 3 to 100 phr, or from 5 to 80 phr. The plasticizers include all the plasticizers that are known to those skilled in the art, such as aromatic, naphthenic or paraffinic mineral oil plasticizers, for example MES (mild extraction solvate), RAE (residual aromatic extract), TDAE (treated distillate aromatic extract), rubber-to-liquid oils (RTL), biomass-to-liquid oils (BTL), for example those having a content of polycyclic aromatics of less than 3% by weight according to method IP 346, rapeseed oil, factices, plasticizer resins that are not among the tackifying resins mentioned, or liquid polymers having a mean molecular weight (determination by GPC=gel permeation chromatography, in accordance with BS ISO 11344: 2004) between 500 and 20,000 g/mol. If additional liquid polymers are used as plasticizers in the disclosed rubber mixtures, these are not counted as rubber in the calculation of the composition of the polymer matrix.

The expression phr (parts per hundred parts of rubber by weight) used in this text is the standard unit of amount for blend recipes in the rubber industry. The dosage of the parts by weight of the individual substances is always based here on 100 parts by weight of the total mass of all rubbers present in the mixture.

The vulcanization of the disclosed sulfur-crosslinkable rubber mixtures is conducted in the presence of sulfur and/or sulfur donors with the aid of vulcanization accelerators, it being possible for some vulcanization accelerators to act simultaneously as sulfur donors. The accelerator can be one or more of thiazole accelerators, mercapto accelerators, sulfenamide accelerators, thiocarbamate accelerators, thiuram accelerators, thiophosphate accelerators, thiourea accelerators, xanthogenate accelerators, and/or guanidine accelerators.

The sulfenamide accelerators including N-cyclohexyl-2-benzothiazolesulfenamide (CBS), N,N-dicyclohexylbenzothiazole-2-sulfenamide (DCBS), benzothiazyl-2-sulfenomorpholide (MBS), and/or N-tert-butyl-2-benzothiazylsulfenamide (TBBS) can also be employed herein.

Sulfur-donating substances used can be any of the sulfur-donating substances known to those skilled in the art. Exemplary sulfur-donating substances include thiuram disulfides, for example tetrabenzylthiuram disulfide (TBzTD), tetramethylthiuram disulfide (TMTD), tetraethylthiuram disulfide (TETD), thiuram tetrasulfides, for example dipentamethylenethiuram tetrasulfide (DPTT), dithiophosphates, for example DipDis (bis(diisopropyl)thiophosphoryl disulfide), bis(O,O-2-ethylhexylthiophosphoryl) polysulfide (e.g. Rhenocure SDT 50®, Rheinchemie GmbH), zinc dichloryldithiophosphate (e.g. Rhenocure ZDT/S®, Rheinchemie GmbH), zinc alkyldithiophosphate, 1,6-bis(N,N-dibenzylthiocarbamoyldithio)hexane, diaryl polysulfides, and/or dialkyl polysulfides.

Further network-forming systems as obtainable, for example, under the Vulkuren®, Duralink® or Perkalink® trade names or network-forming systems as described in U.S. Pat. App. Pub. No. 2010108239 A1 can also be used in the rubber mixture.

The disclosed sulfur-crosslinkable rubber mixtures can be used to produce a motor vehicle tire. Thus, also disclosed are motor vehicle tires, the production of which involves using at least one sulfur-crosslinkable rubber mixture as disclosed herein—comprising at least one copolymer disclosed herein, and prepared by at least one process disclosed herein.

As used herein, the term "motor vehicle tire" is understood to mean a pneumatic motor vehicle tire and a solid rubber tire, including tires for industrial and construction site vehicles, cars, trucks, and bicycle tires.

In an exemplary embodiment, the tire is a pneumatic motor vehicle tire.

In this context, use in all tire components is conceivable in principle, such as, more particularly, the tread, the sidewall, and/or in at least one inner component.

Inner tire components include, for instance, the squeegee, inner liner, core profile, breaker belt, shoulder, breaker belt profile, carcass, bead reinforcement, bead profile, flange profile, and bandage.

Rubber mixtures for the inner tire components and the sidewall are also referred to as body mixture.

In one embodiment, for instance, the disclosed rubber mixtures are incorporated into treads of motor vehicle tires, for instance in the cap of treads with cap/base construction.

Treads make a considerable contribution to the abrasion characteristics and rolling resistance of the motor vehicle tire. In addition, treads in particular have to be crack-resistant.

For use in motor vehicle tires, the disclosed mixtures are, for instance, brought into the shape of a tread, for instance at least into the shape of a tread cap, as a finished mixture prior to vulcanization, and applied in the known manner in the production of the motor vehicle tire blank. However, the tread, for instance at least the tread cap, can also be rolled up in the form of a narrow strip of rubber mixture onto a tire blank. In the case of two-part treads (upper part: cap and lower part: base), the rubber mixtures disclosed herein can be used both for the cap and for the base.

The production of the disclosed rubber mixtures for use as body mixture in motor vehicle tires is carried out as described above for the tread. The difference lies in the shaping after the extrusion operation or the calendering of the disclosed mixtures. The shapes of the as yet unvulcanized rubber mixture for one or more different body mixtures that are obtained in this way then serve for the construction of a tire blank.

The tire blank is then vulcanized under conditions known in the prior art.

The disclosed sulfur-crosslinkable rubber mixtures described herein, therefore, can be employed for the production of a cord, belt, or hose.

For use of the disclosed rubber mixtures in belts, cords, and hoses, especially in conveyor belts, the extruded, as yet unvulcanized mixture is converted to the appropriate shape and, if appropriate, frequently provided at the same time or subsequently with strengthening members, for example synthetic fibers or steel cords. This usually gives rise to a multilayer construction of this kind, consisting of one or more plies of rubber mixture, one or more plies of identical or different strengthening members and one or more further plies of the same or another rubber mixture.

It is understood that the foregoing description is that of the various exemplary embodiments and that additional changes and modifications can be made thereto without departing from the spirit and scope of the description as defined in the appended claims.

What is claimed is:

1. A monomer of formula I):

A—S—P    I)

wherein:
A is a 4-vinylbenzyl group,
S is a sulfur atom,
P is a protecting group selected from the group consisting of: $S(=O)_2-R^1$, $S-C(=S)-N-R^2R^3$, and $N-R^5R^6$,
$R^1$=alkyl, benzyl, or phenyl,
$R^2$ and $R^3$=alkyl, benzyl, or phenyl,
$R^5$=hydrogen atom (H), alkyl, benzyl, or phenyl, and
$R^6$=alkyl, benzyl or phenyl.

2. The monomer of claim 1, wherein the monomer is 4-vinylbenzyl benzenethiosulfonate.

3. A process for preparing a copolymer, which comprises:
free-radical copolymerization of the monomer of claim 1 with at least one further monomer selected from the group consisting of: alkenes, dienes, vinyl compounds, and vinylidene compounds.

4. The process of claim 3, wherein the alkene is selected from the group consisting of: ethene, propene, butene, pentene, and hexene, wherein the diene is selected from the group consisting of: 1,3-butadiene, 2-methylbuta-1,3-diene, 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene, 1,3-cyclooctadiene, and 2-chloro-1,3-butadiene, and wherein the vinyl compound is an acrylate, methacrylates, acrylic acid, methacrylic acid, and/or acrylonitrile, or wherein the vinyl compound is styrene, 2-methylstyrene, 3-methylstyrene, 4-methylstyrene, 2,4-dimethylstyrene, 2,4,6-trimethylstyrene, alpha-methylstyrene, 2,4-diisopropylstyrene, 4-tert-butylstyrene, stilbene, vinylbenzyldimethylamine, 4-vinylbenzyl dimethylaminoethyl ether, N,N-dimethylaminoethylstyrene, tert-butoxystyrene, vinylpyridine, 1,2-divinylbenzene, 1,3-divinylbenzene, and/or 1,4-divinylbenzene.

5. A process for preparing the monomer of claim 1, which comprises:
reacting 4-vinylbenzyl chloride with sodium benzenethiosulfonate in a polar solvent with a phase transfer catalyst.

* * * * *